US007759480B2

(12) United States Patent
Krotz et al.

(10) Patent No.: US 7,759,480 B2
(45) Date of Patent: *Jul. 20, 2010

(54) CHLORAL-FREE DCA IN OLIGONUCLEOTIDE SYNTHESIS

(75) Inventors: Achim Krotz, San Diego, CA (US); Daniel C. Capaldi, Carlsbad, CA (US); Hans-Joachim Josef Gaus, Carlsbad, CA (US); Brett Turney, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 461 days.

This patent is subject to a terminal disclaimer.

(21) Appl. No.: 11/668,174

(22) Filed: Jan. 29, 2007

(65) Prior Publication Data

US 2007/0123703 A1    May 31, 2007

Related U.S. Application Data

(63) Continuation of application No. 10/403,692, filed on Mar. 31, 2003, now Pat. No. 7,169,916.

(60) Provisional application No. 60/369,295, filed on Apr. 1, 2002.

(51) Int. Cl.
    *C07H 21/00* (2006.01)
(52) U.S. Cl. .................. 536/25.3; 536/25.33; 536/25.34
(58) Field of Classification Search .................. None
    See application file for complete search history.

(56) References Cited

U.S. PATENT DOCUMENTS

| | | | |
|---|---|---|---|
| 3,687,808 A | 8/1972 | Merigan, Jr. et al. |
| 3,884,785 A | 5/1975 | Hoelle |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| RE34,069 E | 9/1992 | Koster et al. |
| 5,175,273 A | 12/1992 | Bischofberger et al. |
| 5,218,105 A | 6/1993 | Cook et al. |
| 5,223,168 A | 6/1993 | Holt |
| 5,292,928 A | 3/1994 | Miltenberger |
| 5,319,080 A | 6/1994 | Leumann |
| 5,359,044 A | 10/1994 | Cook et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,432,272 A | 7/1995 | Benner |
| 5,434,257 A | 7/1995 | Matteucci et al. |
| 5,446,137 A | 8/1995 | Maag et al. |
| 5,457,187 A | 10/1995 | Gmeiner et al. |
| 5,457,191 A | 10/1995 | Cook et al. |
| 5,459,255 A | 10/1995 | Cook et al. |
| 5,466,786 A | 11/1995 | Buhr et al. |
| 5,484,908 A | 1/1996 | Froehler et al. |
| 5,502,177 A | 3/1996 | Matteucci et al. |
| 5,506,351 A | 4/1996 | McGee |
| 5,514,785 A | 5/1996 | Van Ness et al. |
| 5,519,134 A | 5/1996 | Acevedo et al. |
| 5,521,302 A | 5/1996 | Cook |
| 5,525,711 A | 6/1996 | Hawkins et al. |
| 5,539,082 A | 7/1996 | Nielsen et al. |
| 5,541,307 A | 7/1996 | Cook et al. |
| 5,552,540 A | 9/1996 | Haralambidis |
| 5,567,811 A | 10/1996 | Misiura et al. |
| 5,571,902 A | 11/1996 | Ravikumar et al. |
| 5,576,427 A | 11/1996 | Cook et al. |
| 5,578,718 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |

(Continued)

FOREIGN PATENT DOCUMENTS

| | | |
|---|---|---|
| DE | 610317 | 2/1935 |
| DE | 852997 | 8/1952 |
| WO | WO 90/02749 A1 | 3/1990 |
| WO | WO 00/08044 A1 | 2/2000 |
| WO | WO 02/061138 A1 | 8/2002 |

OTHER PUBLICATIONS

[R] Weygand et al., Preparative Organic Chemistry, Hilgetag et al. (eds.), John Wiley & Sons, Inc., 1972, New York, NY, only pp. 173-174 supplied.*
(S) Perrin et al., Purification of Laboratory Chemicals, Pergamon Press, Long Island City, NY, 1966, only pp. 2-11, 46-51 and 130-131 supplied.*
(T) Blatt, A.H. (ed.), Organic Synthesis, Collective vol. 2, John Wiley & Sons, Inc., New York, NY, 1943, only pp. 180-183 supplied.*
(U) Michael J. Gait, "An Introduction to Modern Methods of DNA Synthesis," Chapter 1 in Oligonucleotide Synthesis—A Practical Approach, M. J. Gait (ed.), IRL Press, Washington, DC, Oct. 1984, only pp. 1-22 supplied.*

(Continued)

*Primary Examiner*—Lawrence E Crane
(74) *Attorney, Agent, or Firm*—ISIS Patent Department

(57) ABSTRACT

A process of manufacturing oligonucleotides includes a 5'-deblocking step in which the 5-blocking group is removed with dichloroacetic acid that is essentially free of chloral. The process is useful for making oligonucleotides that are substantially free of chloral adducts.

13 Claims, No Drawings

U.S. PATENT DOCUMENTS

| | | | |
|---|---|---|---|
| 5,594,121 A | 1/1997 | Froehler et al. | |
| 5,596,091 A | 1/1997 | Switzer | |
| 5,597,909 A | 1/1997 | Urdea et al. | |
| 5,599,797 A | 2/1997 | Cook et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,627,053 A | 5/1997 | Usman et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci et al. | |
| 5,658,873 A | 8/1997 | Bertsch-Frank et al. | |
| 5,670,633 A | 9/1997 | Cook et al. | |
| 5,681,941 A | 10/1997 | Cook et al. | |
| 5,700,920 A | 12/1997 | Altmann et al. | |
| 5,750,692 A | 5/1998 | Cook et al. | |
| 5,763,588 A | 6/1998 | Matteucci et al. | |
| 5,830,653 A | 11/1998 | Froehler et al. | |
| 5,859,221 A | 1/1999 | Cook et al. | |
| 5,959,099 A | 9/1999 | Cheruvallath et al. | |
| 6,005,094 A | 12/1999 | Simon et al. | |
| 6,005,096 A | 12/1999 | Matteucci et al. | |
| 6,007,992 A | 12/1999 | Lin et al. | |
| 6,028,183 A | 2/2000 | Lin et al. | |
| 6,069,243 A | 5/2000 | Scozzari | |
| 6,147,200 A | 11/2000 | Manoharan et al. | |
| 6,172,209 B1 | 1/2001 | Manoharan et al. | |
| 6,242,591 B1 | 6/2001 | Cole et al. | |
| 6,262,241 B1 | 7/2001 | Cook et al. | |
| 6,271,358 B1 | 8/2001 | Manoharan et al. | |
| 6,576,752 B1 * | 6/2003 | Manoharan et al. | 536/23.2 |
| 6,593,466 B1 * | 7/2003 | Manoharan et al. | 536/26.7 |
| 6,639,062 B2 * | 10/2003 | Manoharan et al. | 536/23.1 |
| 6,645,716 B2 * | 11/2003 | Wheeler et al. | 435/5 |
| 7,169,916 B2 * | 1/2007 | Krotz et al. | 536/25.3 |
| 7,173,123 B2 | 2/2007 | Wheeler et al. | |
| 7,446,193 B2 * | 11/2008 | Wheeler et al. | 536/25.3 |
| 2003/0158403 A1 | 8/2003 | Manoharan et al. | |
| 2003/0175906 A1 | 9/2003 | Manoharan et al. | |
| 2003/0207804 A1 | 11/2003 | Manoharan et al. | |

OTHER PUBLICATIONS (V) Atkinson et al., "Solid Phase Synthesis of Oligodeoxynucleotides by the Phosphite-Triester Method," Chapter 3 in Oligonucleotide Synthesis -A Practical Approach, M. J. Gait (ed.), IRL Press, Washington, DC, Oct. 1984, only pp. 35-81 supplied.*

(W) McLaughlin et al., "H. p. I. c. Column Packing Techniques," Appendix II in Oligonucleotide Synthesis—A Practical Approach, M. J. Gait (ed.), IRL Press, Washington, DC, Oct. 1984, only pp. 207-210 supplied.*

(X) Greene and Wuts, "Protective Groups in Organic Synthesis, Second Edition," John Wiley & Sons, New York, NY, 1991, only pp. 60-67 supplied.*

(Y) Aldrich Chemical Co., "Aldrich Advancing Science" Catalog, 2005-2006, Milwaukee, WI, 2005, only pp. 2394-2395 supplied.*

U.S. Appl. No. 10/403,692 Office Communication Mailed Jul. 7, 2005.

U.S. Appl. No. 10/403,692 Office Communication Mailed Feb. 10, 2006.

U.S. Appl. No. 10/059,776 Office Communication Mailed Apr. 18, 2003.

U.S. Appl. No. 10/679,805 Office Communication Mailed Jul. 8, 2005.

U.S. Appl. No. 10/679,805 Office Communication Mailed Feb. 14, 2006.

U.S. Appl. No. 11/670,283 Office Communication Mailed Dec. 10, 2007.

Beaucage et al., "Advances in the Synthesis of Oligonucleotides by the Phosphoramidite Approach" Tetrahedron (1992) 48:2223-2311.

Fodor et al., "Mechanism of the Wallach Rearrangement of Chloral to Dichloroacetic Acid" Chemistry and Industry (1961) p. 1530.

Good Manufacturing Practice Guide for Active Pharmaceutical Ingredients, step 4 version, dated Nov. 10, 2000.

International Search Report for PCT/US02/09781 dated Sep. 4, 2003.

International Search Report for PCT/US02/02503 dated Jun. 5, 2002.

Khorana et al., "Studies on Polynucleotides: Total Synthesis of the Structural Gene for an Alanine Transfer Ribonucleic Acid from Yeast" J. Mol. Biol. (1972) 72:209-217.

Notice of Opposition to European Patent 1356115 dated Aug. 28, 2007.

Roberts et al., Basic Principles of Organic Chemistry (1964), only pp. 427, 436 and 437 supplied.

Supplementary European Search Report for EP 02 70 6042 dated Apr. 20, 2004.

Wright et al., "Large Scale Synthesis of Oligonucleotides via Phosphoramidite Nucleosides and a High-loaded Polystyrene Support" Tetrahedron Letts. (1993) 34:3373-3376.

Altmann, K.-H. et al., "Second generation antisense oligonucleotides: structure-activity relationships and the design of improved signal-transduction inhibitors," *Biochem. Soc. Trans.* (1996) 24:630-637.

Altmann, K.-H. et al., "Second Generation of Antisense Oligonucleotides: From Nuclease Resistance to Biological Efficacy in Animals," *Chimica* (1996) 50:168-176.

Altmann, K.-H. et al., "Second Generation Antisense Oligonucleotides—Inhibition of PKC-a and *c-RAF* Kinase Expression by Chimeric Oligonucleotides Incorporating 6'-Substituted Carbocyclic Nucleosides and 2'-O-Ethylene Glycol Substituted Ribonucleosides," *Nucleosides Nucleotides* (1997) 16(7-9):917-926.

Altschul, S. F. et al., "Basic Local Alignment Search Tool," *J. Mol. Biol.* (1990) 215:403-410.

Alul, R. H. et al., "Oxalyl-CPG: a labile support for synthesis of sensitive oligonucleotide derivatives," *Nucleic Acids Res.* (1991) 19(7):1527-1532.

Atherton, E. et al., "The Polyamide Method of Solid Phase Peptide and Oligonucleotide Synthesis," *Bioorg. Chem.* (1979) 8:351-370.

Atherton, E. et al., "Peptide synthesis. Part 2. Procedures for Solid-phase Synthesis using $N^{\alpha}$-Fluorenylmethoxycarbonylamino-acids on Polyamide Supports. Synthesis of Substance P and of Acyl Carrier Protein 65-74 Decapeptide," *J.C.S. Perkin I* (1981) 538-546.

Baker, B. F. et al., "2'-O-(2-Methoxy)ethyl-modified Anti-intercellular Adhesion Molecule I (ICAM-1) Oligonucleotides Selectively Increase the ICAM-1 mRNA Level and Inhibit Formation of the ICAM-1 Translation Initiation Complex in Human Umbilical Vein Endothelial Cells," *J. Biol. Chem.* (1997) 272(18):11994-12000.

Bayer, E. et al., "A New Support for Polypeptide Synthesis in Columns," *Tetrahedron Letters* (1970) 51:4503-4505.

Beaucage, S. L., "Oligodeoxyribonucleotides Synthesis," *Methods in Molecular Biology* (1993) Agrawal, S. (ed.) Humana Press Inc., Totowa, Chp. 3, 20:33-61.

Berg, R. H. et al., "Long-Chain Polystyrene-Grafted Polyethylene Film Matrix: A New Support for Solid-Phase Peptide Synthesis," *J. Am. Chem. Soc.* (1989) 111(20):8024-8026.

Bonora, G. M. et al., "A Liquid-Phase Process Suitable for Large-Scale Synthesis of Phosphorothioate Oligonucleotides," *Org. Proc. Res. Dev.* (2000) 4:225-231.

Brazma, A. et al., "Gene expression data analysis," *FEBS Lett.* (2000) 480:17-24.

Carulli, J. P. et al., "High Througput Analysis of Differential Gene Expression," *J. Cell. Biochem. Suppl.* (1998) 30/31:286-296.

Celis, J. E. et al., "Gene expression profiling: monitoring transcription and translation products using DNA microarrays and proteomics," *FEBS Lett.* (2000) 480:2-16.

Conte, M. R. et al., "Conformational properties and thermodynamics of the RNA duplex r(CGCAAAUUUGCG)$_2$: comparison with the DNA analogue d(CGCAAATTTGCG)$_2$," *Nucleic Acids Res.* (1997) 25(13):2627-2634.

Crooke, S. T., "Progress in Antisense Therapeutics," *Med. Res. Rev.* (1996) 16(4):319-344.

Damha, M. J. et al., "Hybrids of RNA and Arabinonucleic Acids (ANA and 2'F-ANA) are Substrates of Ribonuclease H," *J. Am. Chem. Soc.* (1998) 120(49):12976-12977.

Daniels, S. B. et al., "Membranes as Solid Supports for Peptide Synthesis," *Tetrahedron Letters* (1980) 30(33):4345-4348.

De Mesmaeker, A. et al., "Antisense Oligonucleotides," *Acc. Chem. Res.* (1995) 28:366-374.

Eckstein, F. (ed.) *Oligonucleotides and Analogues, a Practical Approach* (1991) Oxford University Press, New York, pp. 56-57 and 256-259.

Eichler, J. et al., "Application of Cellulose Paper as Support Material in Simultaneous Solid Phase Peptide Synthesis," *Collect. Czech. Chem. Commun.* (1989) 54:1746-1752.

Englisch, U. et al., "Chemically Modified Oligonucleotides as Probes and Inhibitors," *Angew. Chem. Int. Ed. Eng.* (1991) 30(6):613-629.

Falbe, J. et al., "Römpp Kompakt Basislexikon Chemie," *George Thieme Verlag, Stuttart* (1998) pp. 401 and 531.

Fedoroff, O. Y. et al., "Structure of a DNA:RNA Hybrid Duplex," *J. Mol. Biol.* (1993) 233:509-523.

Flanagan, W. M. et al., "A cytosine analog that confers enhance potency to antisense oligonucleotides," *Proc. Natl. Acad. Sci. USA* (1999) 96:3513-3518.

Freier, S. M. et al., "The ups and downs of nucleic acid duplex stability: structure-stability studies on chemically-modified DNA:RNA duplexes," *Nucleic Acids Res.* (1997) 25(22):4429-4443.

Froehler, B. C., "Oligodeoxynucleotide Synthesis," *Methods in Molecular Biology vol. 20* (1993) Agrawal, S. (ed.), Humana Press Inc., Totowa, pp. 63-80.

Fuchs, B. et al., "Identification of Differentially Expressed Genes by Mutually Subtracted RNA Fingerprinting," *Anal. Biochem.* (2000) 286:91-98.

Gaus, H. et al., "Trichloroacetaldehyde modified oligonucleotides," *Bioorg. Med. Chem. Lett.* (2005) 15:4118-4124.

Geysen, H. M. et al., "Use of peptide synthesis to probe viral antigens for epitopes to a resolution of a single amino acid," *Proc. Natl. Acad. Sci. USA* (1984) 81:3998-4002.

Going, J. J. et al., "Molecular Pathology and Future Developments," *Eur. J. Cancer* (1999) 35(14):1895-1904.

González, C. et al., "Structure and Dynamics of a DNA•RNA Hybrid Duplex with a Chiral Phosphorothioate Moiety: NMR and Molecular Dynamics with Conventional and Time-Averaged Restraints," *Biochem.* (1995) 34(15):4969-4982.

Gorman, J. J., "An Apparatus for Simultaneous Manual Solid-Phase Synthesis of Multiple Peptide Analogs," *Anal. Biochem.* (1984) 136:397-406.

Gravert, D. J. et al., "Organic Synthesis on Soluble Polymer Supports: Liquid-Phase Methodologies," *Chem. Rev.* (1997) 97(2):489-509.

Holm, A. et al., "Multiple Column Peptide Synthesis," *Peptides, Proceedings of the 20$^{th}$ European Peptide Symposium* (1988) Jung, G. et al. (eds.), Walter de Grutyer & Co., Berlin, pp. 208-210.

Horton, N. C. et al., "The Structure of an RNA/DNA Hybrid: A Substrate of the Ribonuclease Activity of HIV-1 Reverse Transcriptase," *J. Mol. Biol.* (1996) 264:521-533.

Houghten, R. A. et al., "General method for the rapid solid-phase synthesis of large numbers of peptides: Specificity of antigen-antibody interaction at the level of individual amino acids," *Proc. Natl. Acad. Sci. USA* (1985) 82:5131-5135.

Jungblut, P. R. et al., "Proteomics in human disease: Cancer, heart and infectious diseases," *Electrophoresis* (1999) 20:2100-2110.

Jurecic, R. et al., "Long-distance DD-PCR and cDNA microarrays," *Curr. Opin. Microbiol.* (2000) 3:316-321.

Kent, S. B. H. et al., "Preparation and Properties of *tert*-Butyloxycarbonylaminoacyl-4-(oxymethyl) phenylacetamidomethyl-(Kel F-g-styrene) Resin, an Insoluble, Noncrosslinked Support for Solid Phase Peptide Synthesis," *Israel J. Chem.* (1978) 17:243-247.

Korte, F. et al., "Notiz zur Synthese des Xanthopterins," *Chemische Berrichte* (1953) 114-116.

Krchnák, V. et al., "Multiple continuous-flow solid-phase peptide synthesis," *Int. J. Peptide Protein Res.* (1989) 33:209-213.

Kroschwitz, J. I. (ed.), "Polynucleotides," *Concise Encyclopedia of Polymer Science and Engineering* (1990) John Wiley & Sons, pp. 858-859.

Krotz, A. H. et al., "Large-Scale Synthesis of Antisense Oligonucleotides without Chlorinated Solvents," *Org. Proc. Res. Dev.* (2000) 4(3):190-193.

Lane, A. N. et al., "NMR assignments and solution conformation of the DNA • RNA hybrid duplex d(GTGAACTT)·r(AAGUUCAC)," *Eur. J. Biochem.* (1993)215:297-306.

Larson, E. J. et al., "Rapid DNA Fingerprinting of Pathogens by Flow Cytometry," *Cytometry* (2000) 41:203-2083.

Larsson, M. et al., "High-throughput protein expression of cDNA products as a tool in functional genomics," *J. Biotech.* (2000) 80:143-157.

Lebl, M. et al., "Simulation of Continuous Solid Phase Synthesis: Synthesis of Methionine Enkephalin and its Analogs," *Peptide Res.* (1989) 2(4):297-300.

Lesnik, E. A. et al., "Relative Thermodynamic Stability of DNA, RNA, and DNA:RNA Hybrid Duplexes: Relationship with Base Compositions and Structure," *Biochem.* (1995) 34(34):10807-10815.

Lin, K.-Y. et al., "Tricyclic 2'-Deoxycytidine Analogs: Syntheses and Incorporation into Oligodeoxynucleotides Which Have Enhanced Binding to Complementary RNA," *J. Am. Chem. Soc.* (1995) 117(13):3873-3874.

Lin, K.-Y. et al., "A Cytosine Analogue Capable of Clamp-Like Binding to a Guanine in Helical Nucleic Acids," *J. Am. Chem. Soc.* (1998) 120(33):8531-8532.

Madden, S. L. et al., "Serial analysis of gene expression: from gene discovery to target identification;" *DDT* (2000) 5(9):415-424.

Martin, P., "Ein neuer Zugang zu 2'-O-Alkylribonucleosiden und Eigenschaften deren Oligonucleotide," *Helv. Chim. Acta* (1995) 78:486-504.

Parr, W. et al., "Solid-Phase Peptide Synthesis on an Inorganic Matrix having Organic Groups on the Surface," *Angew. Chem. Int. Ed.* (1972) 11(4):314-315.

Prashar, Y. et al., "Reads: A Method for Display of 3'-End Fragments of Restriction Enzyme-Digested cDNAs for Analysis of Differential Gene Expression," *Methods in Enzymology* (1999) 303:258-272.

Reese, C. B., "The Chemical Synthesis of Oligo- and Poly-Nucleotides by the Phosphotriester Approach," *Tetrahedron* (1978) 34:3143-3179.

Sanghvi, Y. S., "Heterocyclic Base Modifications in Nucleic Acids and Their Applications in Antisense Oligonucleotides," *Antisense Research and Applications* (1993) Crooke, S. T. et al. (eds.), CRC Press, Boca Raton, pp. 273-288.

Scott, R. P. W. et al., "The Use of Resin Coated Glass Beads in the Form of a Packed Bed for the Solid Phase Synthesis of Peptides," *J. Chromatographic Sci.* (1971) 9:577-590.

Searle, M. S. et al., "On the stability of nucleic acid structures in solution: enthalphy—entropy compensations, internal rotations and reversibility," *Nucleic Acids Res.* (1993) 21(9):2051-2056.

Singh, S. K. et al., "LNA (locked nucleic acids): synthesis and high-affinity nucleic acid recognition," *Chem. Commun.* (1998) 455-456.

Sutcliffe, J. G. et al., "TOGA: An automated parsing technology for analyzing expression of nearly all genes," *PNAS* (2000) 97(5):1976-1981.

To, K.-Y., "Identification of Differential Gene Expression by High Throughput Analysis," *Comb. Chem. High Throughput Screen.* (2000) 3:235-241.

Tregear, G. W. et al., "Graft Copolymers as Insoluble Supports in Peptide Synthesis," *Chemistry and Biology of Peptides* (1972) 175-178.

Vester, B. et al., "LNAzymes: Incorporation of LNA-Type Monomers into DNAzymes Markedly Increased RNA Cleavage," *J. Am. Chem. Soc.* (2002) 124(46):13682-13683.

Van Rietschoten, J. et al., "Simultaneous Synthesis of Two Peptide Analogs on Different Insoluble Supports," *Peptides, Proc. Eur. Pept. Symp. 13$^{th}$* (1975) 113-116.

Wang, J. et al., "Synthesis and binding property of an oligonucleotide containing tetrafluorophenoxazine," *Tetrahedron Lett.* (1998) 39:8385-8388.

Wilds, C. J. et al., "Duplex Recognition by Oligonucleotides Containing 2'-Deoxy-2'-fluoro-D-arabinose and 2'-Deoxy2'-fluoro-D-ribose. Intermolecular 2'-OH-Phosphate Contacts versus Sugar Puckering in the Stabilization of Triple-Helical Complexes," *Bioconjugate Chem.* (1999) 10:299-305.

Wright, P. et al., "Large Scale Synthesis of Oligonucleotides via Phosphoramidite Nucleosides and a High-loaded Polystyrene Support," *Tetrahedron Lett.* (1993) 34(21):3373-3376.

Zhang, J. et al., "PowerBLAST: A New Network BLAST Application for Interactive or Automated Sequence Analysis and Annotation," *Genome Res.* (1997) 7:649-656.

* cited by examiner

CHLORAL-FREE DCA IN OLIGONUCLEOTIDE SYNTHESIS

CROSS-REFERENCE TO RELATED APPLICATIONS

This application claims benefit of U.S. patent application Ser. No. 10/403,692, filed on Mar. 31, 2003, now U.S. Pat. No. 7,169,916, and U.S. provisional application 60/369,295, filed on Apr. 1, 2002, which is explicitly incorporated herein by reference.

FIELD OF THE INVENTION

The present invention is directed to the field of oligonucleotide synthesis. In particular, the present invention is directed to improved oligonucleotide synthetic methods, whereby improved oligonucleotide characteristics are obtained.

BACKGROUND OF THE INVENTION

Oligomeric compounds having the ability to specifically bind natural and synthetic polynucleotides have numerous uses in analytical methods for detection, identification, and quantification of polynucleotides, as primers and probes for amplifying genes and gene products (e.g. the polymerase chain reaction, PCR), in target validation studies and as therapeutics. Oligomeric compounds such as oligonucleotide DNA and RNA have been used successfully to detect natural polynucleotides and polynucleotide products on so-called biochips. Oligomeric compounds can also be used as primers and probes for taq-polymerase in PCR. Various oligonucleotide compounds and derivatives thereof have been successfully employed in gene-silencing, both in vitro and in vivo. Such oligonucleotide compounds and their derivatives include so-called antisense compounds—oligomers capable of specifically binding a gene or gene product, and either directly or indirectly effecting silencing of the gene.

Antisense therapeutics have shown great promise. Antisense therapeutics modulate protein activities by attenuating the concentration of oligonucleotides, especially RNA, involved in protein synthesis. This is in contrast to conventional therapeutic methods, which seek to modulate protein activities by direct interaction between putative drugs and proteins.

In general, antisense methods involve determining the sequence of a coding oligonucleotide (e.g. mRNA) that encodes for a certain protein (sense strand), developing a relatively short oligomer that selectively binds to the sense strand, and introducing the oligomer into the intracellular environment. Antisense methods can predictably silence gene expression through a variety of mechanisms. In one such mechanism, Translation Arrest, the antisense strand blocks translation by competitively binding to the sense strand of mRNA. In another mechanism, an antisense strand containing a stretch of DNA (e.g. phosphorothioate DNA) binds to the sense strand, whereby the DNA-RNA hybrid is recognized by RNAse H, an endonuclease that selectively cleaves the DNA-RNA hybrid, thereby reducing intracellular RNA levels. Another methodology involves the interaction between small double stranded RNA oligomers and mRNA. In such mechanisms, interaction between the RISC complex, the antisense strand of the small double stranded RNA and intracellular mRNA results in cleavage and degradation of the mRNA.

As antisense molecules have become accepted as therapeutic and diagnostic agents, the need to produce oligonucleotides in large quantities, at higher purity, and at decreased per unit cost has increased as well. The most commonly used antisense compounds to date have been phosphodiester oligonucleotides, phosphorothioate oligonucleotides and second generation oligonucleotides having one or more modified ribosyl sugar units, and more recently, ribosyl sugar units. The methods for making these three types of antisense oligomers are roughly similar, and include the phosphotriester method, as described by Reese, *Tetrahedron* 1978, 34, 3143; the phosphoramidite method, as described by Beaucage, in *Methods in Molecular Biology: Protocols for Oligonucleotides and Analogs*; Agrawal, ed.; Humana Press: Totowa, 1993, Vol. 20, 33-61; and the H-phosphonate method, as described by Froehler in *Methods in Molecular Biology: Protocols for Oligonucleotides and Analogs*; Agrawal, ed.; Humana Press: Totowa, 1993, Vol. 20, 63-80. Of these three methods, the phosphoramidite method has become a de facto standard in the industry.

A typical oligonucleotide synthesis using phosphoramidite chemistry (i.e. the amidite methodology) is set forth below. First, a primer support is provided in a standard synthesizer column. The primer support is typically a solid support (supt) having a linker (link) covalently bonded thereto. It is common to purchase the primer support with a first 5'-protected nucleoside bonded thereto.

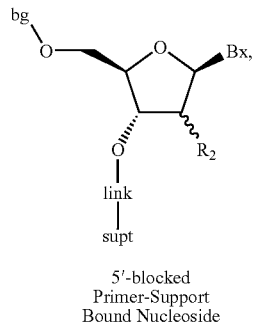

5'-blocked
Primer-Support
Bound Nucleoside

Primer support: bg is a 5'-blocking group, Bx is a nucleobase, $R_2$ is H, OH, OH protected with a removable protecting group, or a 2'-substituent, such as 2'-deoxy-2'-methoxyethoxy (2'-O-MOE), and link is the covalent linking group, which joins the nucleoside to the support, supt.

(A) The 5'-blocking group bg (e.g. 4,4'-dimethoxytrityl) is first removed (e.g. by exposing the 5'-blocked primer-support bound nucleoside to an acid), thereby producing a support-bound nucleoside of the formula:

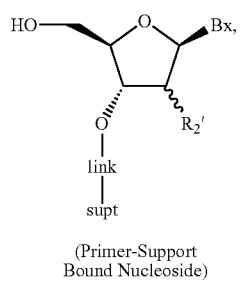

(Primer-Support
Bound Nucleoside)

Activated primer support: wherein supt is the solid support, link is the linking group, Bx is a nucleobase, $R_{2'}$, is H, OH, OH protected with a removable protecting group, or a 2'-substituent.

(B) The column is then washed with acetonitrile, which acts to both "push" the reagent (acid) onto the column, and to wash unreacted reagent and the removed 5'-blocking group (e.g. trityl alcohol) from the column.

(C) The primer support is then reacted with a phosphitylation reagent (amidite), which is dissolved in acetonitrile, the amidite having the formula:

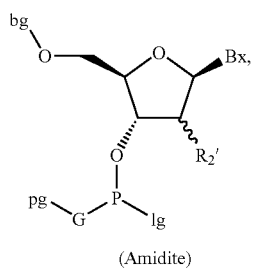

(Amidite)

wherein bg is a 5'-blocking group, 1 g is a leaving group, G is O or S, pg is a phosphorus protecting group, and $R_{2'}$ and Bx have, independent of the analogous variables on the primer support, the same definitions as previously defined.

The product of this reaction is the support-bound phosphite dimer:

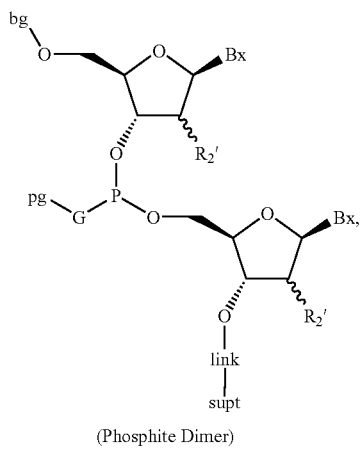

(Phosphite Dimer)

Support-bound wherein each of the variables bg, pg, G, $R_{2'}$ and Bx is independently defined above, link is the linker and supt is the support, as defined above.

(D) The support-bound dimer is then typically washed with acetonitrile.

(E) A capping reagent in acetonitrile is then added to the column, thereby capping unreacted nucleoside.

(F) The column is then washed again with acetonitrile.

(G) The support-bound dimer is then typically reacted with an oxidizing agent, such as a thiolating agent (e.g. phenylacetyl disulfide), in acetonitrile, to form a support-bound phosphate triester:

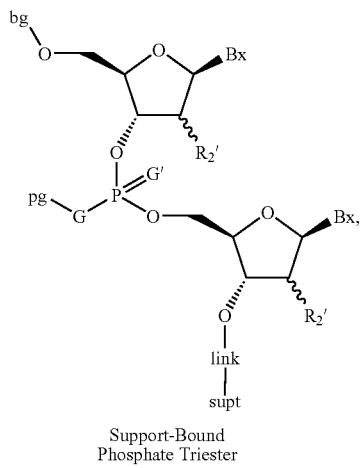

Support-Bound
Phosphate Triester wherein G' is O or S and the other variables are defined herein.

(H) The support-bound phosphate triester is then typically washed with acetonitrile.

Steps (A)-(F) are then repeated, if necessary, a sufficient number of times to prepare a support-bound, blocked oligonucleotide having the formula:

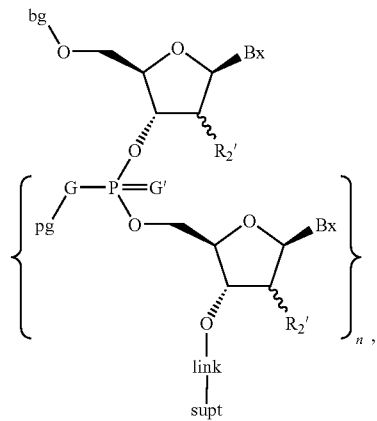

wherein n is a positive integer (typically about 7 to about 79).

The phosphorus protecting groups pg are then typically removed from the oligomer to produce a support-bound oligomer having the formula:

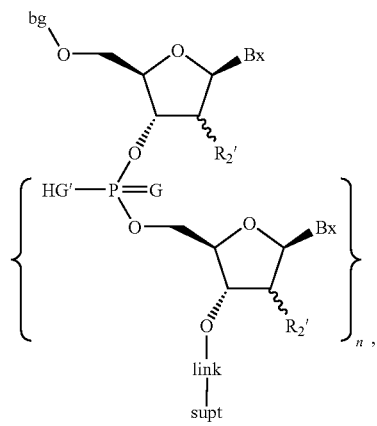

which, after washing with a suitable wash solvent, such as acetonitrile, is typically cleaved from the solid support, purified, 5'-deblocked, and further processed to produce an oligomer of the formula:

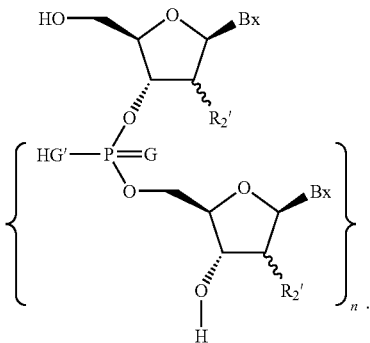

The person having skill in the art will recognize that G'H bound to a P(V) phosphorus is generally is ionized at physiologic pH, and that therefore, wherever G'H appears in the formulae above, or hereafter, G'− is synonymous therewith (the O− or S− being countered by a suitable cation, such as Na+).

A typical blocking group for 5'-protection of nucleotides is the dimethoxytrityl group (DMT). The DMT group is acid labile, and may be removed with relatively weak acid, such as dichloroacetic acid. It is important that the oligonucleotide be produced in both good yield and excellent purity. Yield is commonly expressed in terms of coupling efficiency, which is a measure of the degree to which each successive monomer is coupled to the extant oligonucleotide. Coupling efficiency is affected by a number of factors, including the choice of nucleoside monomers, solvents, temperature, reagents, etc.

Purity is affected by a number of factors, including incomplete coupling (which produces so-called short-mers), as well as the introduction of impurities by reagents, solvents, etc.

It is a goal of oligonucleotide synthesis to produce large quantities of oligonucleotides in excellent yield and purity. Despite advances in the art of oligonucleotide synthesis, there is still a need for synthetic methods the produce oligonucleotides of improved purity.

SUMMARY OF THE INVENTION

The foregoing and further needs are met by embodiments of the present invention, which provide a process of oligonucleotide synthesis comprising a deblocking step, wherein said deblocking step is carried out in the substantial absence of chloral (trichloroacetaldehyde), chloral hydrate, and other derivatives thereof.

The foregoing and further needs are further met by embodiments of the invention, which provide a process of oligonucleotide synthesis, comprising a dichloroacetic acid detritylation step, wherein said detritylation step is carried out in the substantial absence of chloral, its hydrates and other derivatives thereof.

DETAILED DESCRIPTION OF THE INVENTION

The present invention provides improved methods of synthesizing oligonucleotides. In particular, the present invention provides improved methods of deblocking a protected group of a nucleoside during oligonucleotide synthesis. The improved methods of the present invention comprise deblocking the nucleoside in the substantial absence of chloral ($Cl_3CCHO$), chloral hydrate ($Cl_3CCH(OH)_2$), and other derivatives of chloral. The present invention leads to oligonucleotides having enhanced purity as compared to oligonucleotides produced by previously known methodologies. The present invention furthermore leads to oligonucleotides in enhanced yields as compared to prior art methods.

The inventors have discovered that during normal oligonucleotide synthesis a significant impurity arises out of the coupling of chloral or its derivatives to the nascent oligonucleotide during deblocking of 5'-OH groups. Such deblocking is generally referred to as detritylation, because the trityl group, or DMT, is the most commonly used group for protecting the 5'-OH of the nucleoside during coupling of the nucleoside to the oligonucleotide. The most commonly used reagent for detritylation is dichloroacetic acid (DCA).

The inventors have discovered that even very small amounts of chloral impurity in DCA can lead to significant impurities arising from coupling of chloral to or within the oligonucleotide chain. In this context, the term "chloral impurity" is intended to encompass chloral, chloral hydrate, other chloral derivatives present in DCA, and/or mixtures thereof. In contrast, when DCA that is substantially free of chloral impurity is used as a detritylating reagent, the chloral adducts can be significantly reduced or eliminated.

The present invention therefore contemplates deblocking a blocked oligonucleotide in the substantial absence of chloral, its hydrates and other derivatives thereof. In particular the present invention contemplates detritylation in the substantial absence of chloral, its hydrates and other derivatives thereof. More particularly, the present invention provides for detritylation in the presence of a dichloroacetic acid solution in the substantial absence of chloral impurity.

The present invention also contemplates deblocking reagents that are substantially free of chloral impurity. In particular, the present invention contemplates detritylating reagents that are substantially free of chloral impurity. More particularly, the present invention provides dichloroacetic acid that is free of chloral impurity.

The present invention also contemplates oligonucleotides that are substantially free of chloral adducts, as described herein.

Common oligonucleotide synthesis is carried out by the phosphoramidite process taught by Caruthers et al. (U.S. Pat. Nos. 4,458,066, 4,500,707, 5,132,418, 4,415,732, 4,668,777 and 4,973,679) and Köster et al. (see e.g. U.S. Reissue 34,069). The phosphoramidite process generally includes a deblocking step for each cycle of chain extension, in which the 5'-OH is deblocked. In commercial production, the most commonly used blocking group for the 5'-OH group is the 4,4'-dimethoxytriphenylmethyl (DMT) group, which is generally removed by treating the growing oligonucleotide with an acid, e.g. dichloroacetic acid.

The present inventors are the first to have recognized that the deblocking step gives rise to certain adducts that are difficult to remove from the final oligomer product. In particular, the present inventors have determined that the adducts of chloral, chloral hydrate or other chloral derivatives are produced during the detritylation step when chloral impurity is present in the acid used to remove the DMT group from the oligonucleotide.

The physical properties of the chloral adducts are similar to those of the desired oligonucleotide products, which makes separation of chloral adducts from the desired oligonucleotide difficult.

The present inventors have surprisingly discovered that a very small amount of chloral hydrate can have a significant impact on the purity and yield of the desired oligonucleotide product. In fact, concentrations of as little as 0.03 wt. % chloral hydrate (based on weight of 3% v/v DCA solution in toluene) can lead to significant chloral hydrate adducts in the oligonucleotide product.

The inventors have prepared dichloroacetic acid (DCA) that is lower in chloral impurity than commercially available DCA. Reduced chloral impurity DCA was prepared by vacuum distillation. DCA fractions containing chloral impurity below the limit of detection were used in oligonucleotide synthesis. The used of such reduced chloral impurity DCA resulted in oligonucleotide product of significantly improved purity.

Other art recognized methods may be used to prepare reduced chloral impurity DCA, however vacuum distillation is preferred for its scalability. As it has been found that as little as 0.03 wt. % of chloral hydrate in DCA can lead to significant occurrence of chloral adducts, it is desirable to use DCA that contains significantly less than 0.03 wt. % chloral hydrate. In certain embodiments according to the present invention, DCA containing chloral impurity below the limit of detection are used in the deblocking (e.g. detritylating) step of oligonucleotide synthesis.

The present invention provides excellent purity and coupling efficiency of oligonucleotide produced in oligonucleotide synthesis. While the invention has been described with reference to certain preferred embodiments, it is to be understood that other embodiments are possible within the scope of the present invention.

Oligonucleotides

The basic subunit of an oligonucleotide, such as RNA or DNA is depicted below.

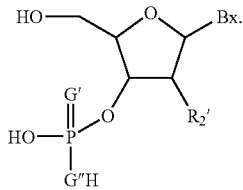

In an oligonucleotide, Bx serves as the Binding Member, as described above, the phosphate moiety [P(=G')(G"H)OH] serves as the Linking Member, and the residue, referred to as the sugar backbone, is the Backbone Member. The phosphate member forms covalent bonds by condensation with the 5'-OH of an adjacent subunit, thereby forming a phosphate diester bond. Where each of G' and G" is O, this is called a phosphodiester bond; where one of G' or G" is S and the other is O, this is called a phosphorothioate bond, and where both G' and G" are S, this is called a phosphorodithioate bond.

One skilled in the art will recognize that in naturally occurring nucleotides, $R_{2'}$ is H for DNA (deoxyribonucleic acid) and OH for RNA (ribonucleic acid), each of G' and G" is O and Bx is one of the following structures:

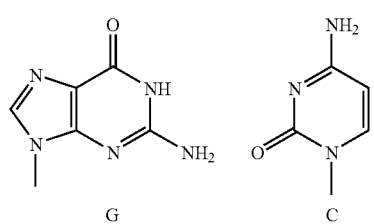

-continued

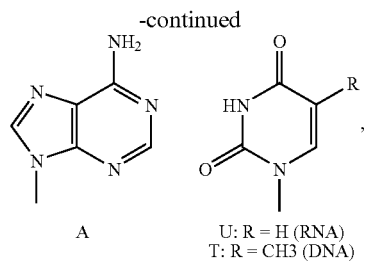

wherein G, C, A, U and T are guanine, cytosine, adenine, thymine and uracil, respectively.

In the above formula, G' and G" may be O or S, and $R_{2'}$ may be H, OH or some other value.

In naturally occurring RNA, the binding member is a nucleosidic base selected from G, C, A and U, and the backbone comprises a sugar residue (ribosyl, i.e. $R_{2'}$ is OH) and a phosphate (G'=G"=O). The ribosyl sugar residue is the backbone member, while the phosphate joins adjacent monomers through the 5'- and 3'-oxygen atoms on the ribosyl ring. The sugar is covalently bound to the nucleosidic base (base) at the 1'-position, the -β-D configuration predominating.

Naturally occurring DNA is analogous to RNA, except that the sugar is a 2'-deoxyribosyl ($R_{2'}$ is H).

Generally oligonucleotides according to the present invention include naturally occurring and non-naturally occurring oligonucleotides. In general, oligonucleotides according to the present invention include compounds of the formula (1):

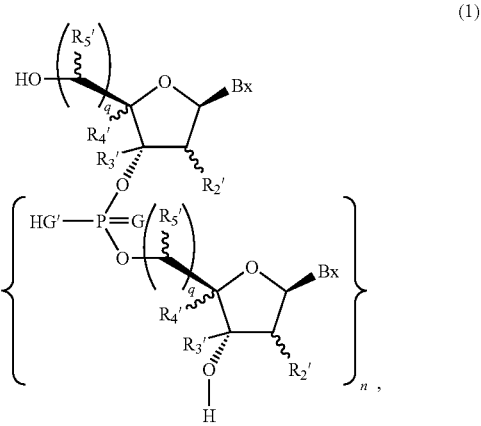

(1)

wherein each Bx is a nucleobase as defined herein, each q is 0 or 1, each of $R_{2'}$ is H, OH, reversibly-protected OH or a substituent or together with $R_{4'}$ forms a bridge; $R_{3'}$ is H or a substituent; $R_{4'}$ is H, a substituent or together with $R_{2'}$ or $R_{5'}$ forms a bridge; $R_{5'}$ is H, a substituent or together with $R_{4'}$ forms a bridge, and each squiggly bond ( ⌇ ) indicates that the bond may be in the up or down configuration.

The naturally occurring oligonucleotides are those in which each of Bx is selected from the group consisting of G, C, A, U (for RNA) and T (DNA), each of G' and G" is O, each $R_{3'}$, each $R_{4'}$, each $R_{5'}$ is H, each q is 1 and n is an integer, and the sugar oxygens are in the ribosyl configuration. Conversely, non-naturally occurring oligonucleotides include those in which at least one of the following conditions applies: At least one Bx is a nucleobase other than a member selected from the groups consisting of G, C, A, U (for RNA) and T (DNA), at least one of G' and G" is other than O, at least one $R_{3'}$, $R_{4'}$, or $R_{5'}$ is other than H, at least at least one q is 0, or at least one of the sugar oxygens is in other than the ribosyl configuration. As used herein, the term "oligonucleotide" encompasses both naturally occurring oligonucleotides and non-naturally occurring oligonucleotides, or mixtures thereof. In specific embodiments of the present invention, the term oligonucleotide refers to a non-naturally occurring oligonucleotide having both naturally-occurring and non-naturally-occurring nucleotide subunits. In specific embodiments of the invention, one or more nucleobases, sugar backbones and/or phosphate linking members are non-naturally-occurring. These features will be described in greater detail below.

Sugar Backbone

In general, the sugar backbone has the structure:

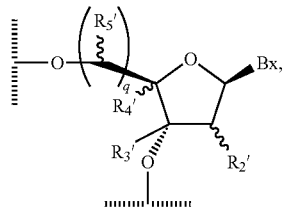

wherein each Bx is a nucleobase as defined herein, q is 0 or 1, each of $R_{2'}$ is H, OH, reversibly-protected OH or a substituent or together with $R_{4'}$ forms a bridge; $R_{3'}$ is H or a substituent; $R_{4'}$ is H, a substituent or together with $R_{2'}$ or $R_{5'}$ forms a bridge; $R_{5'}$ is H, a substituent or together with $R_{4'}$ forms a bridge. The dashes (""""""") indicate the positions at which the sugar moiety is bound to a phosphate linker to form a nucleotide bond.

The person skilled in the art will recognize that when $R_{2'}$ is in the down configuration and q' is 1, the ring is a ribosyl ring, whereas when $R_{2'}$ is in the up configuration and q' is 1, the ring is an arabinosyl ring. Likewise, when q' is 0 and $R_{2'}$ is in the down configuration, the ring is an erythrosyl ring. When $R_{2'}$ and $R_{4'}$ are joined to form a bridge, the ring is called a locked nucleic acid (LNA), as described in greater detail herein. In some embodiments, the bridge formed by $R_{2'}$ and $R_{4'}$ is $R_{2'}$—O—$(CH_2)_r$—$R_{4'}$ (wherein r is 1 or 2) or $R_{2'}$—$CH_2$—O—$CH_2$—$R_{4'}$ (the use of $R_{2'}$ and $R_{4'}$ in the sub-formulae indicating the points of attachment.) LNA may be present in either α-L- or β-D-conformation. See Vester et al., "LNAzymes: Incorporation of LNA-Type Monomers into DNAzymes Markedly Increases RNA Cleavage," Journal of the American Chemical Society, 2002, 124, 13682-3. Each of these analogs possesses a number of useful characteristics, including resistance to exonuclease activity, induction if endonuclease activity (e.g. by RNAse H, the RISC complex, etc.) and modulation of hybridization.

When $R_{4'}$ and $R_{5'}$ form a bridge, they may form, along with the sugar ring to which they are attached, a tricyclic ring. Tricyclic nucleosides of the structure:

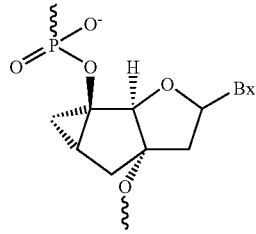

are described by Rennenberg et al. in Nucleic Acids Research, 30(13), 2751-7 (2002). One skilled in the art will recognize that the analogous phosphorothioates, and 2'-substituted tricyclic deoxynucleosides may be prepared by methods analogous to those taught by Rennenberg et al., as modified by the teaching herein. In particular, the phosphorothioates may be prepared by substituting a sulfurizing oxidant (a.k.a. a sulfur transfer reagent, such a phenyl acetyl disulfide) for the oxidizing agent taught by Rennenberg et al. The 2'-substituted tricyclic deoxynucleosides may be prepared from the analogous 2'-substituted deoxynucleosides, using a 2'-OH protecting group in the case of ribonucleic acid.

Certain oligonucleotides that utilized arabino-pentofuranosyl nucleotides as building blocks have been described. Damha et. al., J.A.C.S., 1998, 120, 12976-12977; and Damha et. al., Bioconjugate Chem., 1999, 10, 299-305.

Suitable 2'-substituents corresponding to $R_{2'}$ include: F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification is 2'-deoxy-2'-methoxyethoxy (2'-O—$CH_2CH_2OCH_3$, also known as 2'-O-(2-methoxyethyl) or 2'-MOE ribosyl) (Martin et al., Helv. Chim. Acta, 1995, 78, 486-504). Other preferred modifications include 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula $I_a$ or $II_a$:

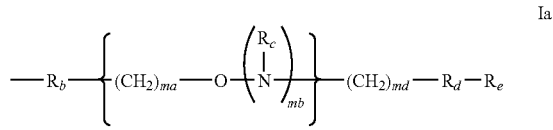

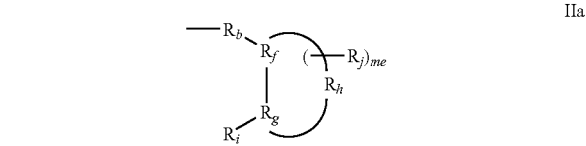

wherein:
$R_b$ is O, S or NH;
$R_d$ is a single bond, O or C(=O);
$R_e$ is $C_1$-$C_{10}$ alkyl, $N(R_k)(R_m)$, $N(R_k)(R_n)$, N=$C(R_p)(R_q)$, N=$C(R_p)(R_r)$ or has formula $III_a$;

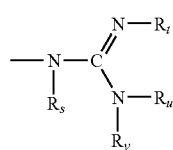

IIIa each $R_c$, $R_q$, $R_r$, $R_s$, $R_t$, $R_u$ and $R_v$ is, independently, hydrogen, $C(O)R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_t$ is hydrogen, a nitrogen protecting group or —$R_x$—$R_y$;
$R_p$ is hydrogen, a nitrogen protecting group or —$R_x$—$R_y$;
$R_x$ is a bond or a linking moiety;
$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, $C(=NH)N(H)R_u$, $C(=O)N(H)R_u$ or $OC(=O)N(H)R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;

ma is 1 to about 10;
mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, now U.S. Pat. No. 6,172,209, entitled "Capped 2'-Oxyethoxy Oligonucleotides." Representative cyclic substituent groups of Formula II are disclosed in U.S. patent application Ser. No. 09/123,108, filed July 27, 1998, now U.S. Pat. No. 6,271,358, entitled "RNA Targeted 2'-Modified Oligonucleotides that are Conformationally Preorganized."

Particularly preferred sugar substituent groups include $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10.

Some preferred oligomeric compounds of the invention contain at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, now U.S. Pat. No. 6,639,062, entitled "Aminooxy-Functionalized Oligomers and Methods for Making Same."

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, and commonly owned U.S. patent application Ser. No. 08/468,037, filed on Jun. 5, 1995.

Representative guanidino substituent groups that are shown in formula III and IV are disclosed in co-owned U.S. patent application Ser. No. 09/349,040, entitled "Functionalized Oligomers", filed Jul. 7, 1999.

Representative acetamido substituent groups are disclosed in U.S. Pat. No. 6,147,200. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-O-methyl and 2'-O-methoxyethyl as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

RNA exists in what has been termed "A Form" geometry while DNA exists in "B Form" geometry. In general, RNA: RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., *Med. Res. Rev.*, 1996, 16, 319-344; De Mesmaeker et al., *Acc. Chem. Res.*, 1995, 28, 366-374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

One synthetic 2'-modification that imparts increased nuclease resistance and a very high binding affinity to nucleotides is the 2'-methoxyethoxy (MOE, 2'-OCH$_2$CH$_2$OCH$_3$) side chain (Baker et al., *J. Biol. Chem.*, 1997, 272, 11944-12000; Freier et al., *Nucleic Acids Res.*, 1997, 25, 4429-4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429-4443). 2'-O-methoxyethyl-substituted oligonucleotides also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, they display improved RNA affinity and higher nuclease resistance. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watsor-Crick base pairing rules with generally improved selectivity compared to the corresponding unmodified reference strands. LNAs may be in either the α-L- or the β-D-conformation. Vester et al., J.A.C.S, 124 (2002) 13682-13683.

LNAs in which the 2'-hydroxyl group is linked to the 4' carbon atom of the sugar ring thereby forming a 2'-C,4'-C-oxymethylene linkage thereby forming a bicyclic sugar moiety. The linkage is preferably an alkylene (($-CH_2-$)$_n$)

group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-$CH_2OCH_2$-4' bridge.

Nucleobases

The nucleobases Bx (also referred to in the art as nucleic acid bases or simply as bases) may be naturally-occurring G, C, A, U or T, or may be selected from a wide range of non-naturally occurring bases as described herein. The two most common classes of nucleobases are purines and pyrimidines. The naturally-occurring purine bases are guanine (G) and adenine (A), which are linked to the sugar through the 9-N nitrogen in the β-anomeric position on the sugar ring. The naturally-occurring pyrimidine bases are uracil (U), thymine (T) and cytidine (C), which are linked to the sugar through the 1-N nitrogen. In double stranded DNA (dsDNA), Watson-Crick base pairing occurs between G and C, and between A and T, whereas in double stranded RNA (dsRNA), Watson-Crick base pairing occurs between G and C, and between A and U. The Watson-Crick base pairs for DNA and RNA are shown below.

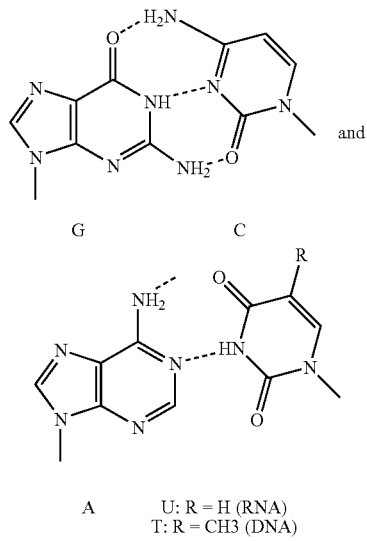

A    U: R = H (RNA)
     T: R = CH3 (DNA)

Analogous base pairing is generally observed in RNA-DNA hybrids, as well as in hybrids between naturally-occurring RNA or DNA and synthetic oligonucleotides comprising non naturally occurring monomeric subunits.

In synthetic oligonucleotides according to the invention, such as antisense therapeutics and diagnostics, one or more of the naturally-occurring nucleobases may be replaced by an analogous binding member (nucleobase analog). Thus, the term "nucleobase" encompasses both naturally-occurring and non-naturally-occurring nucleobases. The term "nucleobase analog" (also referred to herein is a nucleobase mimetic or a nucleic acid base mimetic) refers to non-naturally-occurring nucleobases, and means a residue that functions like a nucleobase by providing sequence specific binding to a heterocyclic residue on a complementary oligomer. In some embodiments according to the invention, a nucleobase analog is a residue that is capable of establishing one or more non-covalent bonds with a nucleobase on a separate oligonucleotide strand. Non-covalent bonds are hydrogen bonds, ionic bonds and polar interactions. (Additional interactions with non-complementary nucleobases are also possible, such as base-stacking interactions). In some embodiments of the invention, non-covalent bonds are formed by hydrogen bonding between nucleobase ring constituents and/or exocyclic substituents, and may be analogous to Watson-Crick bonding, Hoogsteen bonding, some combination thereof, or some other regime as described herein or as known in the art.

As used herein, "unmodified" or "natural" nucleobases mean the purine bases adenine (A) and guanine (G), and the pyrimidine bases thymine (T), cytosine (C) and uracil (U). Modified nucleobases (nucleobase analogs) include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine, 7-propynyl-7-deaza-8-azaguanine, 7-propynyl-7-deaza-8-azaadenine. Further modified nucleobases include tricyclic pyrimidines such as phenoxazine cytidine (1H-pyrimido[5,4b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273;

5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, and U.S. Pat. No. 5,750,692.

In general, the term "base" includes the term nucleobase as described above. The term "base" means a binding member, as described hereinabove. While nucleobases are generally heterocyclic moieties, the term "base" as used herein with means any moiety or residue capable of participating in specific binding to a naturally-occurring nucleobase.

In some embodiments of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications selectively bind to guanosines. Hence they have been termed G-clamps or cytidine analogs. Many of these polycyclic heterocyclic compounds have the general formula:

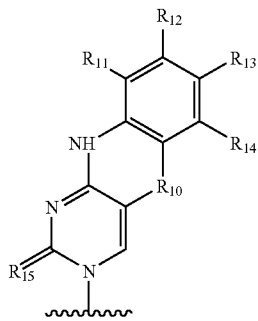

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., Nucleosides and Nucleotides, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155, 920, now U.S. Pat. App. Pub. No. 2003-0207804 A1; and U.S. patent application entitled "Nuclease Resistant Chimeric Oligonucleotides" filed May 24, 2002, Ser. No. 10/013,295, now U.S. Pat. App. Pub. No. US 2003-0175906 A1). $R_{15}$ in these structures is typically O but can also be S.

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a$\Delta T_m$ of up to 18° relative to 5-methyl cytosine (dC5$^{me}$), which is the highest known affinity enhancement for a single modification, yet.

On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999. Such compounds include those having the formula:

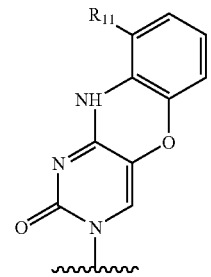

wherein $R_{11}$ includes $(CH_3)_2N$—$(CH_2)_2$—O—; $H_2N$—$(CH_2)_3$—; Ph-$CH_2$—O—C(=O)—N(H)—$(CH_2)_3$—; $H_2N$—; Fluorenyl-$CH_2$—O—C(=O)—N(H)—$(CH_2)_3$—; Phthalimidyl-$CH_2$—O—C(=O)—N(H)—$(CH_2)_3$—; Ph-$CH_2$—O—C(=O)—N(H)—$(CH_2)_2$—O—; Ph-$CH_2$—O—C(=O)—N(H)—$(CH_2)_3$—O—; $(CH_3)_2N$—N(H)—$(CH_2)_2$—O—; Fluorenyl-$CH_2$—O—C(=O)—N(H)—$(CH_2)_2$—O—; Fluorenyl-$CH_2$—O—C(=O)—N(H)—$(CH_2)_3$—O—; $H_2N$—$(CH_2)_2$—O—$CH_2$—; $N_3$—$(CH_2)_2$—O—$CH_2$—; $H_2N$—$(CH_2)_2$—O—, and $NH_2C$(=NH)NH—.

Also disclosed are tricyclic heterocyclic compounds of the formula:

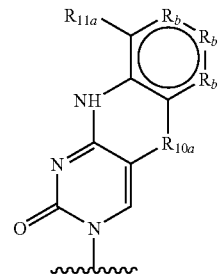

wherein
$R_{10a}$ is O, S or N—$CH_3$;
$R_{11a}$ is $A(Z)_{x1}$, wherein A is a spacer and Z independently is a label bonding group bonding group optionally bonded to a detectable label, but $R_{11a}$ is not amine, protected amine, nitro or cyano;
X1 is 1, 2 or 3; and
$R_b$ is independently —CH=, —N=, —C($C_{1-8}$ alkyl)= or —C(halogen)=, but no adjacent $R_b$ are both —N=, or two adjacent $R_b$ are taken together to form a ring having the structure:

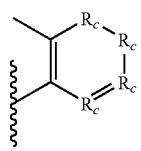

where $R_c$ is independently —CH=, —N=, —C($C_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20 mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

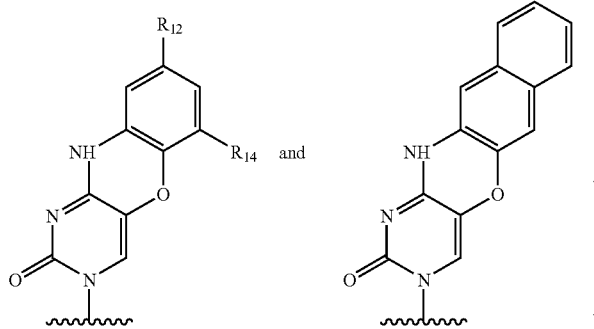

wherein $R_{14}$ is $NO_2$ or both $R_{14}$ and $R_{12}$ are independently —$CH_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997.

Further tricyclic heterocyclic compounds amenable to the present invention also disclosed in the "257, 177 and 269" Patents include those having the formula:

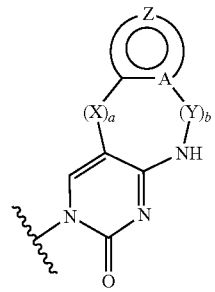

a and b are independently 0 or 1 with the total of a and b being 0 or 1;

A is N, C or CH;

X is S, O, C=O, NH or $NCH_2$, $R^6$;

Y is C=O;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single 0 and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least I non-bridging ring carbon atom is substituted with $R^{20}$ or =O;

or Z is taken together with A to form an aryl ring structure comprising 6 ring atoms wherein the aryl ring carbon atoms are unsubstituted with other than H or at least 1 non-bridging ring carbon atom is substituted with $R^6$ or =O;

$R^6$ is independently H, $C_{1-6}$ alkyl, $C_{2-6}$ alkenyl, $C_{2-6}$ alkynyl, $NO_2$, $N(R^3)_2$, CN or halo, or an $R^6$ is taken together with an adjacent Z group $R^6$ to complete a phenyl ring;

$R^{20}$ is, independently, H, $C_{1-6}$ alkyl, $C_{2-6}$ alkyl, $C_{2-6}$ alkenyl, $C_{2-6}$ alkynyl, $NO_2$, $N(R^{21})_2$, CN, or halo, or an $R^{20}$ is taken together with an adjacent $R^{20}$ to complete a ring containing 5 or 6 ring atoms, and tautomers, solvates and salts thereof;

$R^{21}$ is, independently, H or a protecting group;

$R^3$ is a protecting group or H; and tautomers, solvates and salts thereof.

More specific examples included in the "257, 177 and 269" Patents are compounds of the formula:

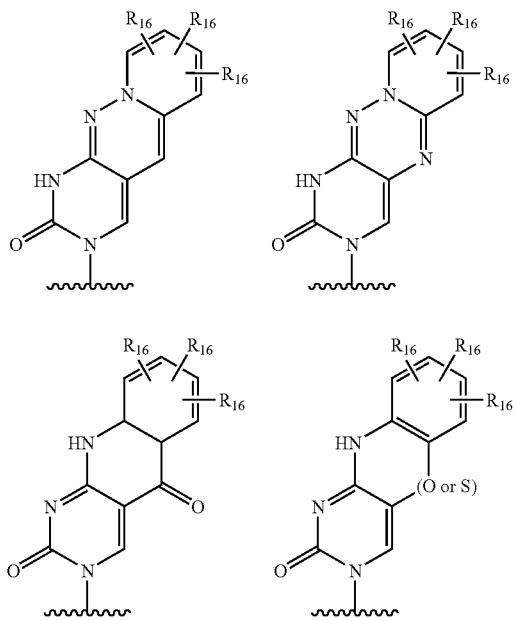

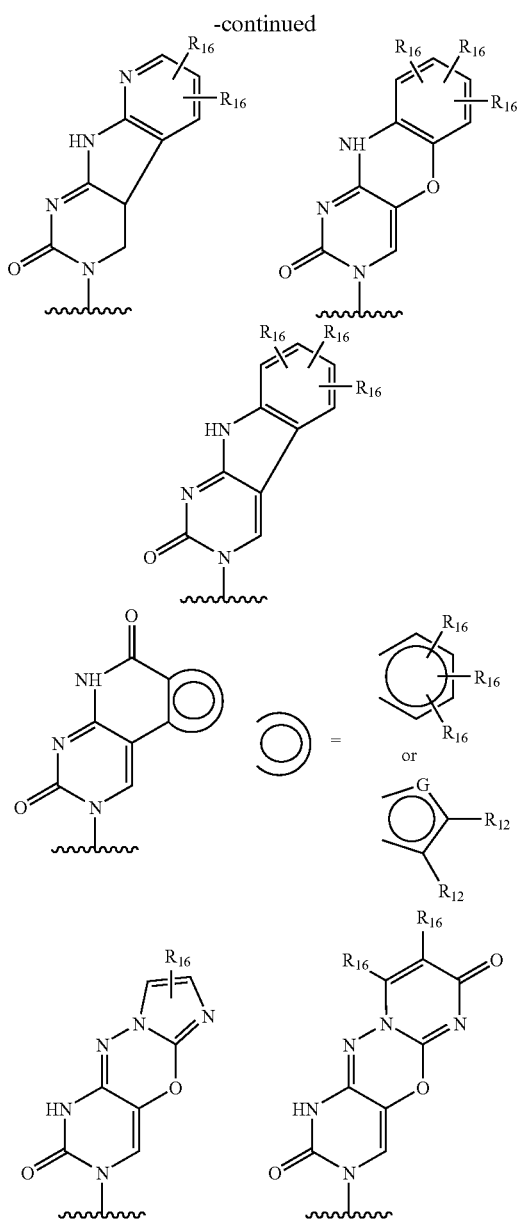

wherein each $R_{16}$, is, independently, selected from hydrogen and various substituent groups.

Further polycyclic base moieties having the formula:

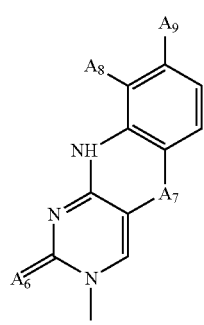

wherein:

$A_6$ is O or S;

$A_7$ is $CH_2$, N—$CH_3$, O or S;

each $A_8$ and $A_9$ is hydrogen or one of $A_8$ and $A_9$ is hydrogen and the other of $A_8$ and $A_9$ is selected from the group consisting of:

$$-O-(CH_2)_{p1}-G \quad \text{and} \quad -O-\left((CH_2)_{p1}-N\begin{pmatrix}\\Q_2\end{pmatrix}\right)_{p2}-Q_1$$

wherein:

G is —CN, —$OA_{10}$, —$SA_{10}$, —N(H)$A_{10}$, —ON(H)$A_{10}$ or —C(NH)N(H)$A_{10}$;

$Q_1$ is H, —NH$A_{10}$, —C(=O)N(H)$A_{10}$, —C(=S)N(H)$A_{10}$ or —C(=NH)N(H)$A_{10}$;

each $Q_2$ is, independently, H or Pg;

$A_{10}$ is H, Pg, substituted or unsubstituted $C_1$-$C_{10}$ alkyl, acetyl, benzyl, —$(CH_2)_{p3}NH_2$, —$(CH_2)_{p3}N(H)Pg$, a D or L α-amino acid, or a peptide derived from D, L or racemic α-amino acids;

Pg is a nitrogen, oxygen or thiol protecting group;

each p1 is, independently, from 2 to about 6;

p2 is from 1 to about 3; and p3 is from 1 to about 4;

are disclosed in U.S. patent application Ser. No. 09/996,292 filed Nov. 28, 2001, now U.S. Pat. App. Pub. No. 2003-0158403 A1.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

Phosphate Linkers

Oligonucleotides are generally those oligomers in which the monomeric subunits comprise linking members having pentavalent phosphorus as a constituent part. Phosphate linkers include phosphodiester, phosphorothioate and phosphorodithioate linkers.

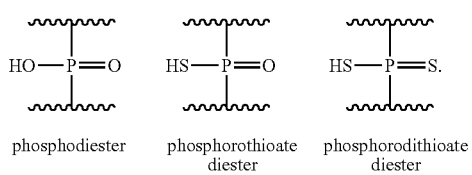

phosphodiester    phosphorothioate    phosphorodithioate
                  diester             diester wherein the squiggles ($\sim$) indicate covalent bonds to backbone members, e.g. oxygen atoms on sugar backbone moieties, or other substituent on sugar analogs.

Oligonucleotides as defined herein generally include salts, solvates and tautomers of oligonucleotides. In general, many bases, especially nucleobases, can form tautomeric structures that are included within the general definitions of oligonucleotides according to the present invention. In addition, the phosphorothioate linker can form the following tautomers:

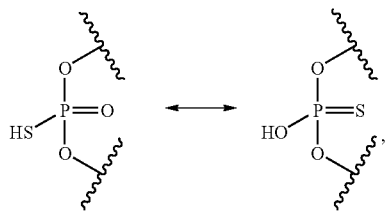

and can likewise form the following salt structures:

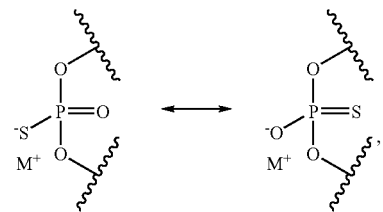

wherein $M^+$ is a suitable salt-forming cation, such as $Na^+$, $K^+$, $\frac{1}{2}Ca^{2+}$, $\frac{1}{2}Mg^{2+}$, $\frac{1}{3}Al^{3+}$, $NH_4^+$, $H_3O^+$, etc. (The fractions indicate fractional equivalents of the cationic species per phosphate diester linkage.) Phosphodiester and phosphorodithioate moieties can form analogous salts.

Naturally occurring nucleosides are linked to one another via a phosphodiester linker. Antisense compounds may be prepared using phosphodiester linkers, which are generally suitable for diagnostic and other nuclease-free uses. However, antisense therapeutic compounds advantageously comprise at least one phosphorothioate linker, owing to the latter's superior nuclease stability. Both phosphodiester and phosphorothioate diester linkers are generally referred to as phosphate diester linkers. When a plurality of nucleotides are linked by successive phosphate diester linkers, the resulting oligomer is called an oligonucleotide.

Manufacture of Oligonucleotides

As described above, the term "oligonucleotide" encompasses naturally-occurring RNA and DNA as well as phosphate-linked oligomers having a variety of sugar backbones and nucleobases. Oligonucleotides have been made by the phosphate triester, H-phosphonate and phosphoramidite methods as described hereinabove. Of these three methods, the phosphoramidite method has become the de facto standard for oligonucleotide synthesis, especially where one or more modifications are made to the sugar backbone or nucleobases, or where exceptional purity, yield or scale are paramount. The phosphoramidite method (amidite method) is described hereinafter.

Amidite Method

Oligonucleotides according to embodiments of the present invention are represented by formula 1, above.

While the present invention is concerned primarily with oligonucleotides, some oligonucleotide mimetics may, with appropriate changes to the starting materials, also be prepared by processes according to the present invention. Oligonucleotide mimetics include compounds in which the oligonucleotide sugar has been replaced with a heterocyclic or carbocyclic ring structure. Such compounds are depicted in Formula 1a, below.

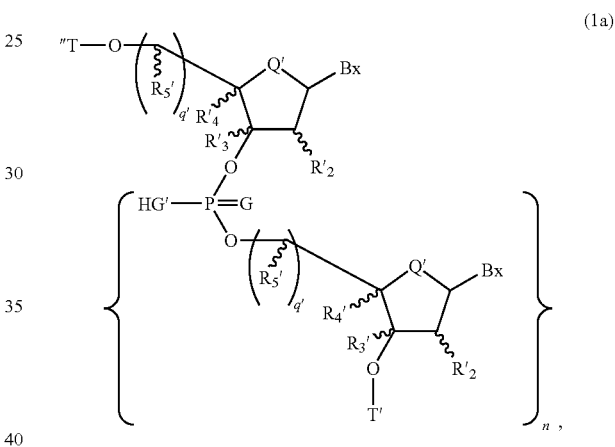

(1a)

and tautomers, salts and solvates thereof, wherein G, G', Bx, n, $R_2'$, $R_3'$, $R_4'$ and $R_5'$ each have the meanings previously defined. The groups T' and T'" are each H, or conjugate groups, such as protecting groups and substituents. Each Q' is independently O, S, $NR'''$, $C(R''')_2$, or $-CR'''=CR'''-$, where each R''' is H, alkyl, or where two R''' groups are on the same or adjacent carbon atoms, they may form a carbocyclic or heterocyclic ring, wherein the ring contains one or two of N, O or S. Preferred values of R''' are H and $C_1$-$C_4$ alkyl.

The foregoing oligonucleotides and oligonucleotide mimetics may be manufactured by solid phase synthesis, e.g. by the amidite method. Equipment for such synthesis is sold by several vendors including, for example, Applied Biosystems (Foster City, Calif.). Other means for such synthesis known in the art may additionally or alternatively be employed. For example stirred bed reactors have been used.

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos.

4,415,732; 4,458,066; 4,500,707; 4,668,777; 4,973,679; and 5,132,418; and Köster U.S. Pat. No. 4,725,677 and Re. 34,069.

Examples of the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, issued Jun. 29, 1993, and 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, now U.S. Pat. No. 6,262,241, and U.S. Pat. No. 5,459,255, drawn to, inter alia, methods of synthesizing 2'-fluoro-oligonucleotides.

The amidite method of oligonucleotide synthesis may be carried out generally in the following manner: Phosphoramidites are prepared by reacting a suitable nucleoside or modified nucleoside (formula 4) with a phosphorodiamidite (formula 5) to form a phosphoramidite (formula 6):

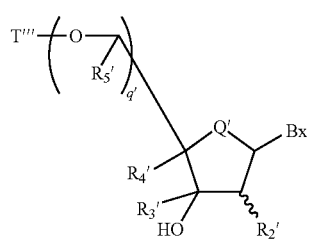

(4)

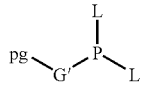

(5)

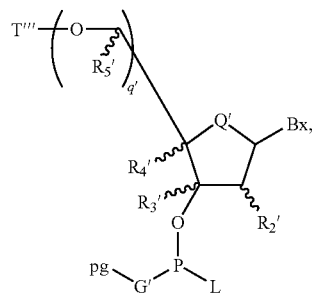

(6)

wherein each of the variables Q', Bx, $R_2'$, $R_3'$, $R_4'$, $R_5'$, G', and q' is as previously defined. L is an amine leaving group; pg is a phosphorus protecting group; and T''' is a hydroxyl protecting group, each as more specifically defined herein. In some embodiments of the present invention, in at least one cycle of the synthetic method, T''' is DMT.

A support-bound nucleoside of Formula 7 is first deprotected at the 5'-position (resulting in a free 5'-OH group). In some embodiments of the present invention, at least one of the 5-protecting groups (T''') is DMT, and the deprotecting reagent is dichloroacetic acid (DCA). In more specific embodiments of the present invention, a plurality of 5'-deprotection steps are carried out in the presence of DCA. In certain embodiments of the present invention, each of the 5'-deprotection steps is carried out in the presence of DCA. In this context, DCA is substantially free of chloral, chloral hydrate, or other derivatives of chloral. In some embodiments, the DCA is tested by HPLC or other suitable method and contains no chloral, chloral hydrate or other derivative of chloral above the limit of detection.

After 5'-deprotection, a first amidite (7) is coupled to a support-bound nucleoside to form a support-bound dimer of Formula 8, which is then oxidized, and subjected to a capping step to form a support bound dimer of Formula 9.

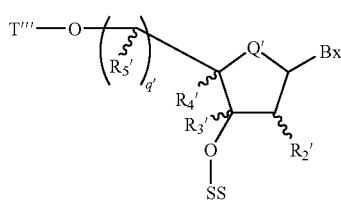

(7)

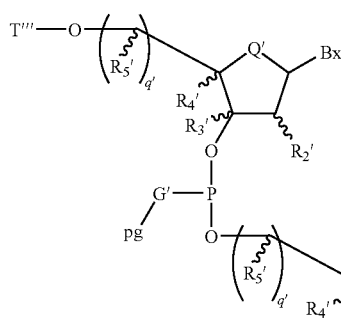

(8)

-continued

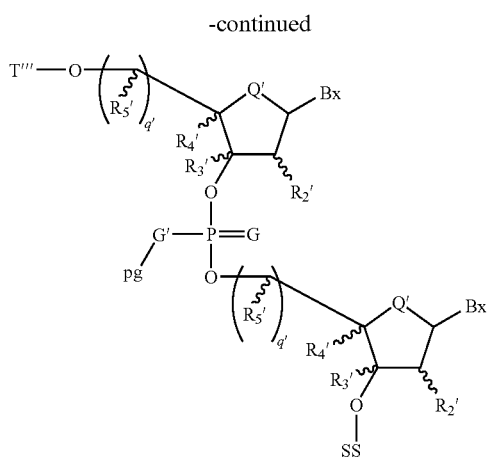

(9)

The 5'-deprotection, coupling, oxidation and capping steps are then repeated n-2 times to form a support-bound oligomer of Formula 10.

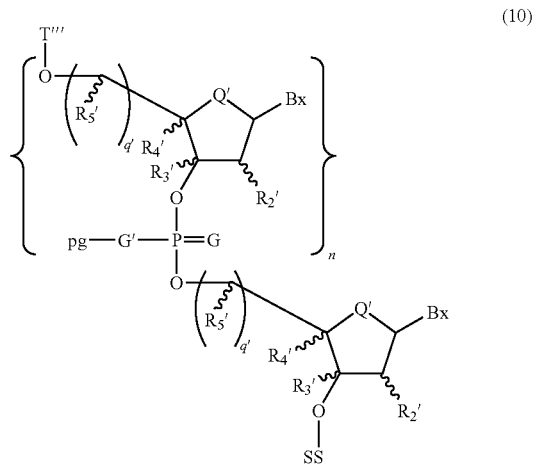

(10)

This compound (10) is then cleaved from the solid support, 5'-deprotected, if necessary, and purified to yield an oligomer of Formula (1). The oligonucleotide may then be further derivatized, purified, precipitated, or otherwise treated, as described in more detail herein. In select embodiments of the present invention, the final protecting group is left on the oligonucleotide (10, SS replaced by H), which is first subjected to high performance liquid chromatography (HPLC), before the final 5'-protecting group is removed. In specific embodiments of the present invention, the final 5'-protecting group is removed by contacting the purified oligonucleotide with acetic acid. In other embodiments the 5'-protecting group may be removed while the oligonucleotide is left on the solid support (SS). The deprotected oligonucleotide (10, wherein T''' is replaced by H) may then be removed from the column as described above and subjected to purification steps. In specific embodiments of the invention, a deprotected oligonucleotide may be subjected to ion exchange chromatography, such as soft anion exchange (SAX) chromatography. Anion exchange chromatography may be carried out either directly after a deprotected oligonucleotide is removed from the solid synthesis support, or after a 5'-protected oligonucleotide has been purified by liquid chromatography and then deprotected.

In each of the foregoing Formulae, SS represents a support bound to the 3'-terminal nucleoside by a cleavable linker, each pg is a phosphorus protecting group as defined herein, n is an integer, G and G' are independently O or S, and each Bx, $R_2'$, $R_3'$, $R'_4$, $R_5'$, Q', and q' is independently as defined in Formula 3.

Amidites

Phosphoramidites (amidites) used in the synthesis of oligonucleotides are available from a variety of commercial sources (included are: Glen Research, Sterling, Va.; Amersham Pharmacia Biotech Inc., Piscataway, N. J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. RE 34,069).

Support Media

Oligonucleotides are generally prepared, as described above, on a support medium (support), e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support media can be soluble or insoluble, or may possess variable solubility in different solvents to allow the growing support bound polymer to be either in or out of solution as desired. Traditional support media such as solid supports are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support media (support) is intended to include supports known to the person skilled in the art to for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

Further support media amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., J. Am. Chem. Soc., 1975, 97, 6584, Bioorg. Chem. 1979, 8, 351, and J. C. S. Perkin 1538 (1981)).

Other support media amenable to the present invention include without limitation a composite of a resin and another material that is also substantially inert to the organic synthesis reaction conditions employed. One exemplary composite (see Scott, et al., J. Chrom. Sci., 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, Israel J. Chem. 1978, 17, 243 and van Rietschoten in Peptides 1974, Y. Wolman, Ed., Wiley and Sons, New York, 1975, pp. 113-116). Contiguous solid supports other than PEPS, such as cotton sheets (Lebl and Eichler, Peptide Res. 1989, 2, 232) and hydroxypropylacrylate-coated polypropylene membranes (Daniels, et al., Tetrahedron Lett. 1989, 4345). Acrylic acid-grafted polyethylene-rods and 96-microtiter wells to immobilize the growing peptide chains and to perform the compartmentalized synthesis. (Geysen, et al., Proc. Natl. Acad. Sci. USA, 1984, 81, 3998). A "tea bag" containing traditionally-used polymer beads. (Houghten, Proc. Natl. Acad. Sci. USA, 1985, 82, 5131). Simultaneous use of two different supports with different densities (Tregear, Chemistry and Biology of Peptides, J. Meienhofer, ed., Ann Arbor Sci. Publ., Ann Arbor, 1972 pp. 175-178). Combining of reaction vessels via a manifold (Gorman, Anal. Biochem., 1984, 136, 397). Multicolumn solidphase synthesis (e.g., Krchnak, et al., Int. J. Peptide Protein Res., 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., Collect. Czech. Chem. Commun., 1989, 54, 1746). Support mediated synthesis of peptides have also been reported (see, Synthetic Peptides: A User's Guide, Gregory A. Grant, Ed. Oxford University Press 1992; U.S. Pat. Nos. 4,415,732; 4,458,066; 4,500,707; 4,668, 777; 4,973,679; 5,132,418; 4,725,677 and Re-34,069.)

Equipment for Synthesis

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

Phosphorus Protecting Groups

In general, the phosphorus protecting group (pg) is an alkyl group or a β-eliminable group having the formula —$CH_2CH_2$-$G_w$, wherein $G_w$ is an electron-withdrawing group. Suitable examples of pg that are amenable to use in connection with the present invention include those set forth in the Caruthers U.S. Pat. Nos. 4,415,732; 4,458,066; 4,500, 707; 4,668,777; 4,973,679; and 5,132,418; and Köster U.S. Pat. No. 4,725,677 and Re. 34,069. In general the alkyl or cyanoethyl withdrawing groups are preferred, as commercially available phosphoramidites generally incorporate either the methyl or cyanoethyl phosphorus protecting group.

The method for removal of phosphorus protecting groups (pg's) depends upon the specific pg to be removed. The β-eliminable groups, such as those disclosed in the Köster et al. patents, are generally removed in a weak base solution, whereby an acidic β-hydrogen is extracted and the —$CH_2CH_2$-$G_w$ group is eliminated by rearrangement to form the corresponding acrylo-compound $CH_2$=CH-$G_w$. In contrast, an alkyl group is generally removed by nucleophilic attack on the α-carbon of the alkyl group. Such pg's are described in the Caruthers et al. patents, as cited herein.

Oxidation (Including Sulfurization)

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent," and oxidation will be understood to embrace both introduction of oxygen and introduction of sulfur, or sulfurization. Where it is important to indicate that an oxidizing agent introduces an oxygen into a P(III) species to make a P(V) species, the oxidizing agent will be referred to herein is "an oxygen-introducing oxidizing reagent."

Oxidizing reagents for making phosphate diester linkages (i.e. oxygen-introducing oxidizing reagents) under the phosphoramidite protocol have been described by e.g. Caruthers et al. and Köster et al., as cited herein. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis O,O-diisopropoxy phosphinothioyl) disulfide (known as Stec reagent). Oxidizing reagents for making phosphorothioate diester linkages include phenyl acetyl disulfide (PADS), as described by Cole et al. in U.S. Pat. No. 6,242,591. In some embodiments of the invention, the phosphorothioate diester and phosphate diester linkages may alternate between sugar subunits. In other embodiments of the present invention, phosphorothioate linkages alone may be employed.

Various solvents may be used in the oxidation reaction. Suitable solvents are identified in the Caruthers et al. and Köster et al. patents, cited herein. The Cole et al. patent describes acetonitrile as a solvent for phenyl acetyl disulfide. Other suitable solvents include toluene, xanthenes, dichloromethane, etc.

Cleavage and Workup

Reagents for cleaving an oligonucleotide from a support are set forth, for example, in the Caruthers et al. and Köster et al. patents, as cited herein.

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

5'-Deprotection

In general, the 5'-hydroxylprotecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. in the presence of dichloroacetic acid (DCA), trichloroacetic acid (TCA), or acetic acid. Removal of DMT from the support-bound oligonucleotide is generally performed with DCA. In embodiments of the present invention, at least one of the 5'-protecting groups is DMT and the reagent for removing the 5'-protecting group from that nucleotide is DCA. In some embodiments of the invention, a plurality of the 5'-protecting groups is DMT, and the reagents for removing those protecting groups are all DCA, optionally in a suitable solvent, such as acetonitrile or toluene. In still other embodiments of the invention, each of the 5'-protecting group is DMT, and all but the final DMT group is removed on the support using DCA in a suitable solvent as deprotecting reagent, the final DMT group being removed after the oligonucleotide has been cleaved from the support, as described above. In some other embodiments of the invention, each 5'-protecting group is DMT and each 5'-protecting group is removed using DCA while the oligonucleotide is on the solid support.

In some embodiments of the present invention, the last 5'-protecting group may be other than DMT, e.g. pixyl, and the final 5'-protecting group may be removed using an acid other than DCA.

Removal of 5-protection after cleavage of the oligonucleotide from the support is generally performed with acetic acid, however a weaker acid may be used in the case of more labile protecting groups than DMT.

Oligomer Design Considerations

In naturally occurring oligonucleotides, the sugar ring is β-D-ribosyl (RNA) or β-D-2'-deoxyribosyl (DNA). The hybridization behavior of DNA with RNA differs from the hybridization of RNA to RNA. This difference gives rise to different in vitro and in vivo effects. For example, DNA-RNA hybrids effectively bind to RNAse H, which results in scission of RNA. In contrast, RNA-RNA hybrids may be unwound by helicase, whereby the antisense strand is permitted to form a hybrid with mRNA. The exogenous RNA-mRNA hybrid interacts with one or more members of the RISC complex, which effects mRNA scission.

Synthetic sugars and sugar analogs are designed to adopt certain spatial conformations that resemble DNA, RNA or some structure intermediate between these conformations. Again, the sugar or sugar analog functions as a sort of platform to hold the base in the correct orientation to interact with bases on the opposite strand. The sugar or sugar analog (collectively skeletal members) also provides binding sites for the linking groups, which join the monomeric units together to form the oligomer. The conformation of the sugar or sugar analog greatly influences the spatial orientations of the bases and linking groups, and also greatly influences the shape of the antisense-sense hybrid in solution. This conformational influence can have an important impact on the efficacy of the antisense compound in modulation of gene expression.

In the broadest sense, the term "oligonucleotide" refers to an oligomer having a plurality of skeletal members, e.g. sugar units (ribosyl, deoxyribosyl, arabinosyl, modified sugar unit, etc.) linked by phosphate diester linkers (i.e. phosphoryl or thiophosphoryl diester), and having bases for establishing binding to complementary oligomer strands. In some embodiments of the invention, an oligonucleotide may contain both phosphoryl diester and phosphorothioate linkers. In other embodiments, the linkers are all phosphorothioate linkers. While phosphoryl linkers are the naturally occurring type of linkers in oligonucleotides, thiophosphate linkers are known to confer nuclease stability to oligonucleotides cells. Hence, it is often preferred to prepare oligonucleotides with at least a portion of the phosphate diester moieties replaced by phosphorothioate diester moieties.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compounds. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Uses for Oligomers

Oligomers, and especially oligonucleotides and chimeras according to the present invention, have been used in a variety of applications, including in assays, sequence arrays, primers and probes for nucleic acid amplification (e.g. PCR), as antisense molecules for gene target validation and therapeutic applications, etc. The person skilled in the art will recognize understand that the methods according to the present invention may be adapted to prepare oligomers for such applications. Accordingly, only select uses of oligomers according to the present invention will be described herein.

Antisense

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid aid continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Research Reagents, Diagnostics, Kits

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904)

and mass spectrometry methods (reviewed in To, *Comb. Chem. High Throughput Screen*, 2000, 3, 235-41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a particular protein. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a particular protein, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

An antisense compound is specifically hybridizable when binding of the compound to the target DNA or RNA molecule interferes with the normal function of the target DNA or RNA to cause a loss of activity, and there is a sufficient degree of complementarity to avoid nonspecific binding of the antisense compound to non-target sequences under conditions in which specific binding is desired, i.e., under physiological conditions in the case of in vivo assays or therapeutic treatment, and in the case of in vitro assays, under conditions in which the assays are performed. It is preferred that the antisense compounds of the present invention comprise at least 80% sequence complementarity with the target nucleic acid, more that they comprise 90% sequent complementarity and even more comprise 95% sequence complementarity with the target nucleic acid sequence to which they are targeted. Percent complementarity of an antisense compound with a target nucleic acid can be determined routinely using basic local alignment search tools (BLAST programs) (Altschul et al., *J. Mol. Biol.,* 1990, 215, 403-410; Zhang and Madden, *Genome Res.,* 1997, 7, 649-656).

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are specifically hybridizable are hereinbelow referred to as "preferred target regions" and are therefore preferred sites for targeting. As used herein the term "preferred target region" is defined as at least an 8-nucleobase portion of a target region to which an active antisense compound is targeted. While not wishing to be bound by theory, it is presently believed that these target regions represent regions of the target nucleic acid which are accessible for hybridization.

While the specific sequences of particular preferred target regions are set forth below, one of skill in the art will recognize that these serve to illustrate and describe particular embodiments within the scope of the present invention. Additional preferred target regions may be identified by one having ordinary skill.

Target regions 8-80 nucleobases in length comprising a stretch of at least eight (8) consecutive nucleobases selected from within the illustrative preferred target regions are considered to be suitable preferred target regions as well.

Exemplary good preferred target regions include DNA or RNA sequences that comprise at least the 8 consecutive nucleobases from the 5'-terminus of one of the illustrative preferred target regions (the remaining nucleobases being a consecutive stretch of the same DNA or RNA beginning immediately upstream of the 5'-terminus of the target region and continuing until the DNA or RNA contains about 8 to about 80 nucleobases). Similarly good preferred target regions are represented by DNA or RNA sequences that comprise at least the 8 consecutive nucleobases from the 3'-terminus of one of the illustrative preferred target regions (the remaining nucleobases being a consecutive stretch of the same DNA or RNA beginning immediately downstream of the 3'-terminus of the target region and continuing until the DNA or RNA contains about 8 to about 80 nucleobases). One having skill in the art, once armed with the empirically-derived preferred target regions illustrated herein will be able, without undue experimentation, to identify further preferred target regions. In addition, one having ordinary skill in the art will also be able to identify additional compounds, including oligonucleotide probes and primers, that specifically hybridize to these preferred target regions using techniques available to the ordinary practitioner in the art.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, Nucl. Acids Research, 1997, 25, 4429-443).

The person having skill in the art will recognize that further embodiments are possible within the general scope of the foregoing description and the attached drawings and claims, and it would be within the skill of such skilled person to practice the invention as generally described herein.

All references cited herein, including all patents, patent documents, applications, published application, and non-patent references, are expressly incorporated herein by reference.

We claim:

1. A process, comprising:
   subjecting dichloroacetic acid comprising an initial concentration of chloral hydrate, chloral or a mixture thereof to distillation;
   collecting at least one fraction of dichloroacetic acid, said fraction having a lower concentration of below about 0.03 weight % of chloral hydrate, chloral or a mixture thereof relative to said initial concentration; and
   contacting an oligonucleotide comprising a blocked hydroxyl group with at least a portion of said at least one fraction of dichloroacetic acid under conditions suitable to remove said blocking group.

2. The process of claim 1, wherein the lower concentration of chloral hydrate, chloral or a mixture thereof is below the limit of detection for chloral hydrate, chloral or a mixture thereof.

3. The process of claim 1, wherein said blocked hydroxyl group comprises a 4,4'-dimethoxytrityl blocking group.

4. The process of claim 1, wherein said blocked hydroxyl group is a blocked 5'-hydroxyl.

5. The process of claim 1, wherein said distillation comprises vacuum distillation.

6. The process of claim 1, whereby said deblocked oligonucleotide is provided substantially free of chloral hydrate, chloral or a mixture thereof.

7. The process of claim 1, wherein the initial concentration of chloral hydrate, chloral or a mixture thereof and the lower concentration of chloral hydrate, chloral or a mixture thereof is detected by a chromatographic method.

8. The process of claim 7, wherein said chromatographic method is high pressure liquid chromatography.

9. The process of claim 7, wherein said chromatographic method is gas chromatography.

10. The process of claim 1, wherein the oligonucleotide is bound to a solid support.

11. The process of claim 1, wherein said dichloroacetic acid is present in the form of a dichloroacetic acid-containing solution.

12. The process of claim 11, wherein the dichloroacetic acid-containing solution further comprises an arene solvent.

13. The process of claim 12, wherein the arene solvent is toluene.

* * * * *